(12) United States Patent
Colin et al.

(10) Patent No.: US 10,746,662 B2
(45) Date of Patent: Aug. 18, 2020

(54) METHOD AND SYSTEM FOR DETECTING AND MEASURING FLUORESCENCE SIGNALS

(71) Applicant: BIOMÉRIEUX, Marcy-L'Etoile (FR)

(72) Inventors: Bruno Colin, Marcy-L'Etoile (FR);
Laurent Drazek, Grenoble (FR);
Frederic Pinston, Grenoble (FR)

(73) Assignee: BIOMERIEUX, Marcy-L'Etoile (FR)

(*) Notice: Subject to any disclaimer, the term of this patent is extended or adjusted under 35 U.S.C. 154(b) by 0 days.

(21) Appl. No.: 16/211,835

(22) Filed: Dec. 6, 2018

(65) Prior Publication Data

US 2019/0107492 A1    Apr. 11, 2019

Related U.S. Application Data

(62) Division of application No. 14/655,061, filed as application No. PCT/FR2013/053258 on Dec. 23, 2013, now Pat. No. 10,168,284.

(30) Foreign Application Priority Data

Dec. 26, 2012  (FR) .................................... 12 62790

(51) Int. Cl.
*G01N 21/00* (2006.01)
*G01N 21/77* (2006.01)
(Continued)

(52) U.S. Cl.
CPC ........... *G01N 21/77* (2013.01); *G01N 21/645* (2013.01); *G01N 33/5304* (2013.01);
(Continued)

(58) Field of Classification Search
CPC ...................................................... G01N 21/77
(Continued)

(56) References Cited

U.S. PATENT DOCUMENTS 6,537,801 B1    3/2003  Ida et al.
6,635,886 B1 *  10/2003  Rushbrooke ....... G01N 21/6428
                                                    250/458.1
(Continued)

FOREIGN PATENT DOCUMENTS

DE    10344140 A1    4/2005
EP    1253420 A      5/1961
(Continued)

OTHER PUBLICATIONS

International Search Report and Written Opinion dated Apr. 17, 2014 for PCT/FR2013/053258.

*Primary Examiner* — Christine T Mui
*Assistant Examiner* — Emily R. Berkeley
(74) *Attorney, Agent, or Firm* — Oliff PLC (57) ABSTRACT

A method and system incorporating a process for analyzing a sample to be tested to determine the presence of or to quantify an analyte in the sample. The process employs a reaction which produces a reaction medium derived from the sample that possesses fluorescence properties, in response to illumination by a light source. The process includes illuminating the sample and detecting a fluorescent signal, introducing the reaction medium, and illuminating the sample and detecting a second fluorescent signal from the sample. The process further includes processing the two signals to determine which portion of the fluorescent signal is produced solely by the reaction medium.

3 Claims, 9 Drawing Sheets

(51) Int. Cl.
    *G01N 21/64*     (2006.01)
    *G01N 33/53*     (2006.01)
    *G01N 33/536*     (2006.01)

(52) U.S. Cl.
    CPC ... *G01N 33/536* (2013.01); *G01N 2021/7786* (2013.01); *G01N 2201/062* (2013.01)

(58) Field of Classification Search
    USPC .......................................................... 422/82
    See application file for complete search history.

(56) References Cited

U.S. PATENT DOCUMENTS

| | | |
|---|---|---|
| 2003/0008401 A1 | 1/2003 | Berndt |
| 2003/0082516 A1 | 5/2003 | Straus |
| 2003/0138875 A1 | 7/2003 | Powers et al. |
| 2003/0152994 A1 | 8/2003 | Woudenberg et al. |
| 2007/0154938 A1 | 7/2007 | Oshida et al. |

FOREIGN PATENT DOCUMENTS

| | | |
|---|---|---|
| FR | 2887626 A1 | 12/2006 |
| WO | 2012022963 A1 | 2/2012 |
| WO | 2014102502 A1 | 7/2014 |

\* cited by examiner

METHOD AND SYSTEM FOR DETECTING AND MEASURING FLUORESCENCE SIGNALS

CROSS-REFERENCE TO RELATED APPLICATIONS

This application is a divisional application of U.S. patent application Ser. No. 14/655,061 filed on Jun. 24, 2015, and titled "METHOD AND SYSTEM FOR DETECTING AND MEASURING FLUORESCENCE SIGNALS," which is a U.S. national stage filing under 35 U.S.C. § 371 of International PCT Application No. PCT/FR2013/053258 filed Dec. 23, 2013, and titled "METHOD AND SYSTEM FOR DETECTING AND MEASURING FLUORESCENCE SIGNALS," which claims priority to and the full benefit of French Patent Application No. 1262790, filed Dec. 26, 2012, and titled "METHOD AND SYSTEM FOR DETECTING AND MEASURING FLUORESCENCE SIGNALS." The entirety of each is incorporated by reference herein.

TECHNICAL FIELD

The present invention generally relates to a method and a system for detecting and measuring fluorescence signals emitted by a reaction medium, derived from a sample to be tested in order to carry out an analysis of said sample capable of containing analytes. The analytes may be representative of the presence of microorganisms or of an illness which it is desired to detect, characterise or monitor.

PRIOR ART

In the field of analysis of samples capable of containing analytes of interest, the use of methods based on fluorimetric measurements is known, i.e. measurements which make it possible to quantify fluorescence signals emitted during the biological analysis of the sample. The analysis of the sample to be tested must therefore comprise the use of a reagent which is representative of the analyte to be detected or to be quantified in the sample. The reagent makes it possible to obtain a reaction product which possesses fluorescence properties. Indeed, by applying the principle of fluorescence, such a reaction product exposed to a light source, corresponding to a first wavelength referred to as the excitation wavelength, in turn emits light rays in accordance with a second wavelength referred to as the emission wavelength. The medium derived from the sample to be tested and containing the reaction product is then a reaction medium. In this reaction medium, the detection of the fluorescence signals, associated with signal processing of these fluorescence signals, makes it possible to determine, for example, the presence or the concentration of the specific analyte sought within the sample to be tested.

In order to obtain a reliable value of the concentration of the specific analyte, the detection of the fluorescence signals must be performed with precision. During such detection, sources of interference such as particles of matter close to the reaction medium, derived from the sample and comprising the reaction product, can produce interfering fluorescence signals.

Document US 2007/0154938 describes a method for analysing a biological sample, located on a plate, using fluorescence signal measurements. Thus, a light source illuminates the reaction medium derived from the biological sample in order to obtain an emission of fluorescence signals coming from this biological sample. According to document US 2007/0154938, the emissions of fluorescence signals coming from the reaction medium derived from the biological sample are subjected to interference by the emission of fluorescence signals coming from foreign substances located on the plate, in the proximity of the reaction medium. Document US 2007/0154938 proposes to resolve this problem of fluorescence signal interference by avoiding taking into account fluorescence data associated with the location of the foreign substances on the plate. Thus, an average value of the fluorescence signals emitted by the reaction medium is calculated by considering only the fluorescence signals associated with the location of the reaction medium on the plate. The detection and the measurement of the fluorescence signals emitted by the reaction medium are therefore more precise. The analysis of the biological sample is therefore improved.

However, in certain situations, the material of the well containing the reaction medium is also capable of emitting fluorescence signals in response to illumination. These fluorescence signals are also considered to be interference signals vis-à-vis fluorescence signals emitted by the reaction medium. The suppression of these interference signals proves to be complex insofar as the material of the well cannot be distinguished from the reaction medium during the detection and measurement of the fluorescence signals.

STATEMENT OF THE INVENTION

The present invention is aimed at overcoming the above-mentioned problems, at least in part.

A first objective of the invention consists of providing a method of analysing a sample to be tested to determine the presence of or to quantify an analyte capable of being present in said sample, employing a reaction which produces a reaction medium derived from said sample and which possesses fluorescence properties, said reaction medium being located within a well, said reaction medium and said well forming an analysis assembly which possesses fluorescent properties in response to an illumination by a light source which produces a light signal, said light source being movable along a surface S1 of the well, also called first surface S1 of the well, said method comprising the following steps:

illumination of surface S1 of the well by means of the light source, before introduction of the reaction medium into the well from n positions of the light source;

detection of a fluorescence signal from the well, for each position n of the light source, in response to the illumination and before introduction of the reaction medium into the well to produce a first signal;

illumination of the analysis assembly by means of the light source, after introduction of the reaction medium into the well, from the n positions of the light source;

detection of a fluorescence signal from the analysis assembly, for each position n of the light source, in response to the illumination and after introduction of the reaction medium into the well to produce a second signal;

performing a calculation operation comprising the first signal and the second signal to produce a resulting signal corresponding to the emission of the fluorescence signal produced solely by the reaction medium.

According to an embodiment of the invention, the illumination of the well comprises illumination in the air, i.e. before the first edge of the wall of the well, on the first edge of the wall of the well, on the wall of the well, on the second edge of the wall of the well and in the air, i.e. after the second edge of the wall of the well.

According to an embodiment of the invention, the detection of a fluorescence signal comprises the detection of a fluorescence signal from a second surface S2 of the well, opposite the first surface S1.

According to an embodiment of the invention, the resulting signal corresponds to a fluorescence signal emitted by the analyte.

According to an embodiment of the invention, the resulting signal corresponds to a fluorescence signal emitted by the well.

According to an embodiment of the invention, the intensity of the resulting signal is proportional or inversely proportional to the concentration of the analyte in the sample tested.

According to an embodiment of the invention, the light source comprises a light-emitting diode (LED).

According to an embodiment of the invention, the reaction is an antigen-antibody reaction, in particular by immunoenzyme assay.

According to an embodiment of the invention, the step of performing a calculation operation comprises performing an operation of deconvolution of the resulting signal by the lighting profile of the light source to produce a resulting signal corresponding to the emission of the fluorescence signal produced solely by the reaction medium.

Another objective of the invention consists of providing a system of analysing a sample to be tested to determine the presence of or to quantify an analyte capable of being present in said sample, employing a reaction which produces a reaction medium derived from said sample and which possesses fluorescence properties, said reaction medium being located within a well, said reaction medium and said well forming an analysis assembly which possesses fluorescence properties, said system comprising:

an optical device comprising a light source movable along a surface S1 of the well, also called first surface S1 of the well, to illuminate the analysis assembly by means of excitation beams and a detection device to detect the fluorescence emissions coming from the analysis assembly;

a signal processing device for performing a calculation operation on a first signal produced by the optical device, relating to the fluorescence emission coming from the analysis assembly before the introduction of the reaction medium, and a second signal also produced by the optical device, relating to the fluorescence emission coming from the analysis assembly after the introduction of the reaction medium, in order to produce a resulting signal corresponding to the emission of the fluorescence signal produced solely by the reaction medium.

According to an embodiment of the invention, the optical device illuminates the first surface S1 of the well.

According to an embodiment of the invention, the optical device detects the fluorescence emissions coming from a second surface S2 of the well, opposite the first surface S1.

BRIEF DESCRIPTION OF THE DRAWINGS

The invention, its functionality, its applications and its advantages shall be better understood by reading the present description, made with reference to the figures, in which.

DETAILED DESCRIPTION OF THE INVENTION

The detailed description below aims to set out the invention in a manner which is sufficiently clear and complete, notably with the aid of examples, but must by no means be regarded as limiting the scope of protection to the particular embodiments and to the examples presented below. The examples below will enable the present invention to be better understood. Nevertheless, these examples are given merely by way of illustration and must under no circumstances be regarded as limiting the scope of said invention in any way.

The term signal or beam is used in the singular below. However, the present invention relates to a set of fluorescence signals and a set of excitation beams.

The present invention relates to sample analysis. According to the present invention, the sample may be from various origins, for example of food, environmental, veterinary, clinical, pharmaceutical or cosmetic origin.

Amongst the samples of food origin, non-exhaustive mention may be made of a sample of dairy products (yogurts, cheeses . . . ), meat, fish, egg, fruit, vegetable, water, beverages (milk, fruit juice, soda, etc.). Of course, these samples of food origin may also come from sauces or more complex meals, or from unprocessed or partially processed raw materials. A food sample may also be derived from an animal feed, such as oil cakes, animal meals.

As indicated previously, the biological sample may be of environmental origin and may consist, for example, of a surface sample, water sample, etc.

The sample may also consist of a biological sample, of clinical, human or animal origin, which may correspond to specimens of biological fluid (urine, whole blood or derivatives such as serum, plasma, saliva, pus, cerebrospinal fluid, etc.), of stools (for example cholera-induced diarrhea), of specimens from the nose, throat, skin, wounds, organs, tissues or isolated cells. This list is obviously not exhaustive.

Generally, the term "sample" refers to a part or a quantity, and more particularly a small part or a small quantity, sampled from one or more entities for the purposes of analysis. This sample may possibly have undergone pre-treatment, including for example mixture, dilution or even crushing stages, in particular if the starting entity is solid-state.

The analysed sample is likely to contain—or is suspected of containing—at least one analyte representative of the presence of microorganisms or of a disease to be detected, characterised or monitored. The sample analysis employs a reaction between the analyte of interest and one or more binding partner(s) specific to the analyte.

According to an embodiment of the present invention, the reaction is an immunological reaction which involves, as binding partner(s), antigens and/or antibodies, receptors for the analyte and the analyte to be determined is a protein, a peptide or a hapten. As examples of such reactions, mention may be made of so-called "competition reactions" and so-called "sandwich reactions" employed in immunoenzyme assays of the ELISA or ELFA type.

Of course, the term "immuno" in "immunoassay" should not be considered in the present application as strictly indicating that the binding partner is an immunological partner, such as an antibody. Indeed, the Person Skilled in the Art also widely uses this term when the binding partner, also called a ligand, is not an immunological partner but is, for example, a receptor for the analyte to be assayed. Thus, it is known to use the term ELISA (Enzyme-Linked Immunosorbent Assay) for assays which use non-immunological binding partners, more widely called "Ligand Binding Assay" in English, which could be translated into French as "Dosage utilisant la liaison à un ligand", whereas the term "immuno" itself is included in the acronym ELISA. In the interests of clarity, the Applicant shall, in the application, use the term "immuno" for any assaying of a protein analyte, even when it is not an immunological partner.

According to another embodiment of the present invention, the reaction is a hybridisation reaction and the analyte to be determined is a nucleic acid of the DNA or RNA type, namely a reaction which involves a complementary nucleotide fragment of the analyte to be determined.

Of course, the reaction employed during the analysis of the sample to be tested uses a reagent which, in the presence of the analyte to be detected or quantified, is capable of directly or indirectly generating fluorescence. This reagent therefore makes it possible to obtain a reaction product which possesses fluorescence properties. The reaction product is then contained in the reaction medium which is derived from the sample but of which the content is different.

Figure 1:
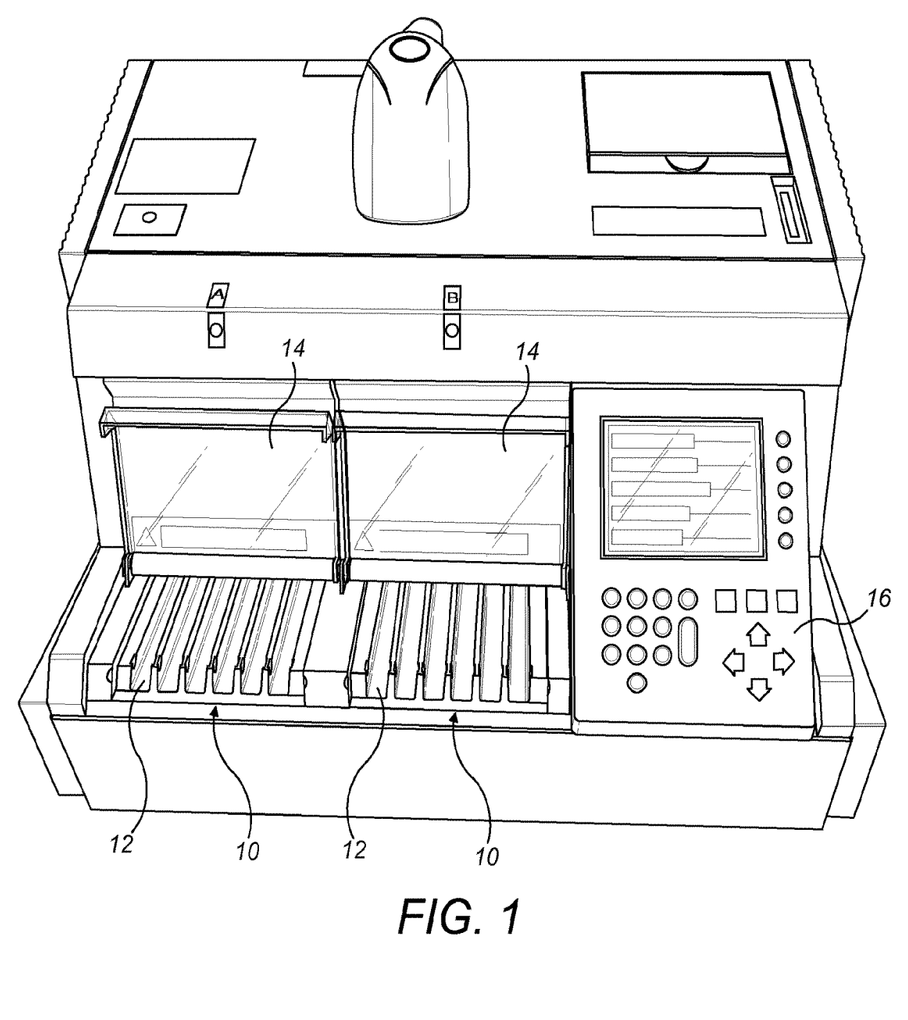
FIG. 1 shows an analysis device for carrying out biological analyses according to an embodiment of the invention, by way of example.

FIG. 1 shows an analysis device 1 for carrying out biological analyses of samples. This analysis device 1 comprises at least one receptacle 10 made up of several rails 12. A movable protective cover 14 is associated with each receptacle 10. Each receptacle 10 comprises a variable number of rails 12, for example from between 1 and 10. FIG. 1 shows 6 rails, for example. Each rail 12 may receive an analysis well strip 20 such as described hereafter in FIG. 2. One rail 12 extends from the exterior of the analysis device 1 to the interior of the analysis device 1.

The analysis device 1 also comprises a user interface 16 in order to launch the program relating to the desired analysis.

Figure 2:
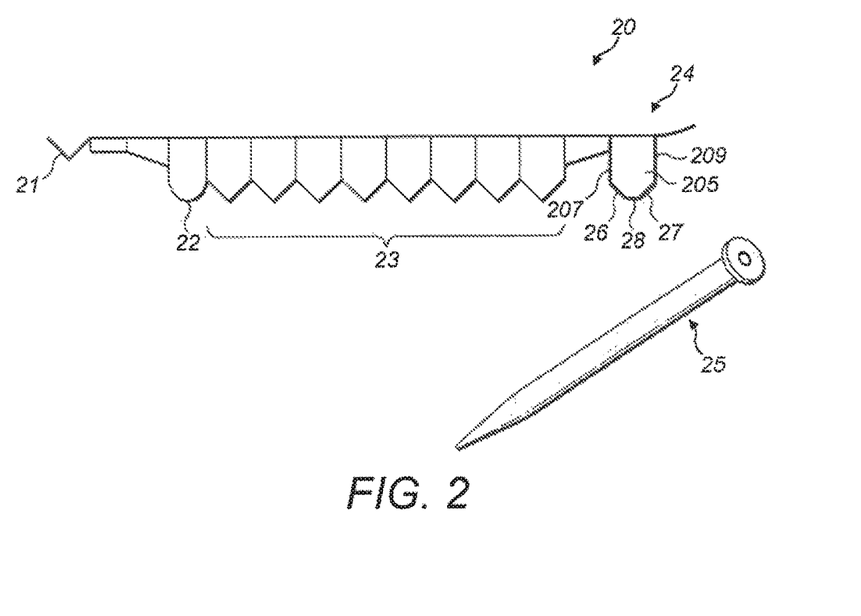
FIG. 2 shows an associated analysis well strip and an associated analysis cone for a biological analysis according to an embodiment of the invention, by way of example.

As shown in FIG. 2, the analysis well strip 20 has a length of approximately 15 cm, greater than the length of a rail 12. The analysis well strip 20 comprises a gripping means 21 in order to facilitate the insertion of the analysis well strip 20 within a rail 12 of the analysis device 1 by a user. The analysis well strip 20 also comprises several wells. A protective film (not shown) located on the upper rim of the wells makes it possible to cover, in a leakproof manner, the various contents of the various wells. Thus, the analysis well strip 20 comprises a first well 22 located at a first end of the analysis well strip 20. The first well 22 comprises for example an oblong-shaped wall. The first well 22 contains the sample to be analysed. A plurality of wells 23 is situated after the first well 22. The wells 23 comprise vertical walls linked by a pyramid-shaped base, with four triangular faces oriented two-by-two facing one another. The wells 23 may also comprise a continuous oblong-shaped wall. Each well 23 contains a solution. The wells 23 contain reagents necessary for the reaction to determine the presence of the analyte to be tested or to quantify the analyte to be tested. In particular, one of the wells 23 contains a reagent which, in the presence of the analyte to be detected or quantified, is capable of generating a reaction product which possesses fluorescence properties if the analyte is present in said sample to be tested. The analysis of the sample is based on this reaction product which is situated in the reaction medium.

Figure 3:
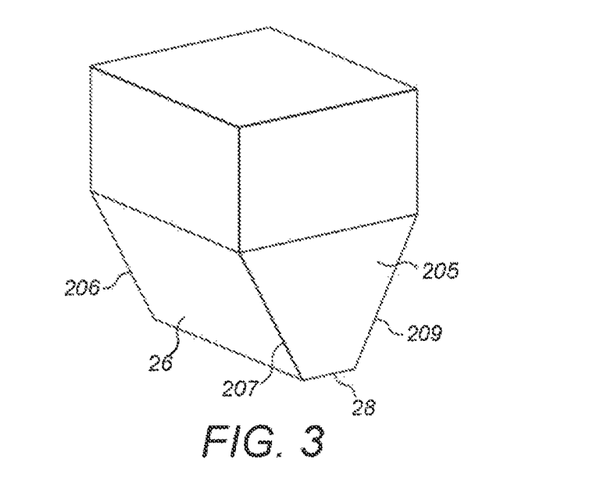
FIG. 3 shows a detailed perspective view of a last the well of the analysis well strip according to FIG. 2, according to an embodiment of the invention, by way of example.
Figure 4:
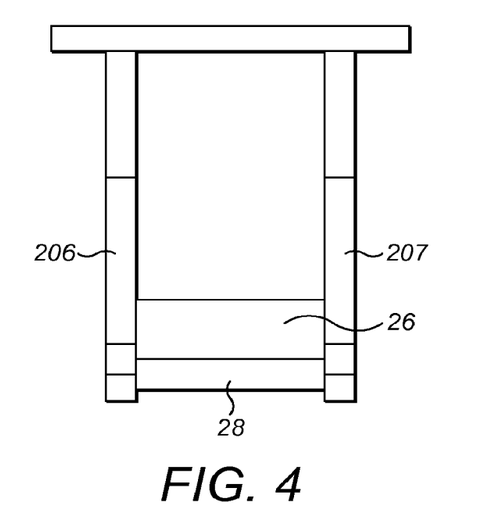
FIG. 4 shows a first lateral view of the last well according to FIG. 3, defining a first surface S1, according to an embodiment of the invention, by way of example.
Figure 5:
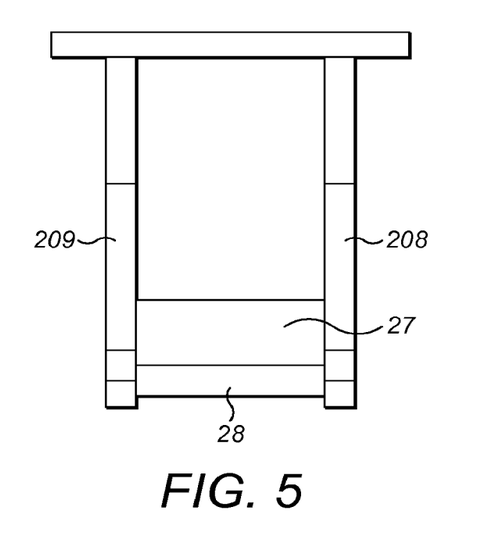
FIG. 5 shows a second lateral view of the last well according to FIG. 3, defining a second surface S2, according to an embodiment of the invention, by way of example.

As shown in FIGS. 2 and 3, the analysis well strip 20 comprises a last well 24 located at the second end of the analysis well strip 20. The last well 24 comprises vertical walls 204 (not shown) and 205 which are around one millimetre thick. Each vertical wall 204, 205 is delimited by respective edges 206, 207, 208, 209 as shown in FIGS. 3, 4, 5, 8, 9 and 11. These edges 206, 207, 208, 209 are also around one millimetre thick, thicker than of the walls 26 and 27. The vertical walls 204 and 205 are linked by a base comprising two inclined walls 26 and 27 connected by a narrow horizontal wall 28 as shown in FIGS. 2 and 3. The walls 26 and 27 are delimited by the vertical walls 204 and 205. Thus, the wall 26 is delimited by the edges 206 and 207. The wall 27 is delimited by the edges 208 and 209. At the end of the analysis cycle, the last well 24 contains a reaction medium comprising various liquids sampled from the wells 22 and 23.

The liquid is transported between the various wells, 22, 23 and 24 by means of an analysis cone 25 shown in FIG. 2. The analysis cone 25 acts as the solid phase for the reaction. Indeed, the analysis cone 25 is covered with at least one binding partner for the analyte. The analysis cone 25 also makes it possible to aspirate liquid from the first well 22 and to discharge the aspirated liquid into another well 23 to obtain a first mixture. The analysis cone 25 then aspirates this first mixture and discharges the first mixture into another well 23 and so on up to the last well 24 into which the reaction medium is discharged. Depending on the type of analysis desired, all or some of the wells 23 may be necessary for analysis of the liquid regarding the sample initially taken from the well 22.

Figure 6:
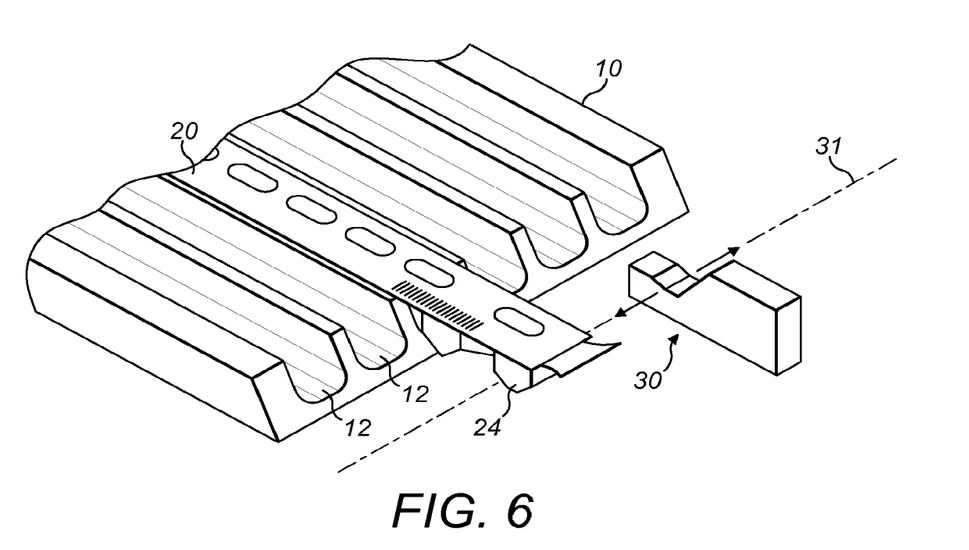
FIG. 6 shows the analysis well strip, according to FIG. 2, positioned within the analysis device according to FIG. 1 and an optical device in the proximity of the analysis well strip, according to an embodiment of the invention, by way of example.
Figure 7:
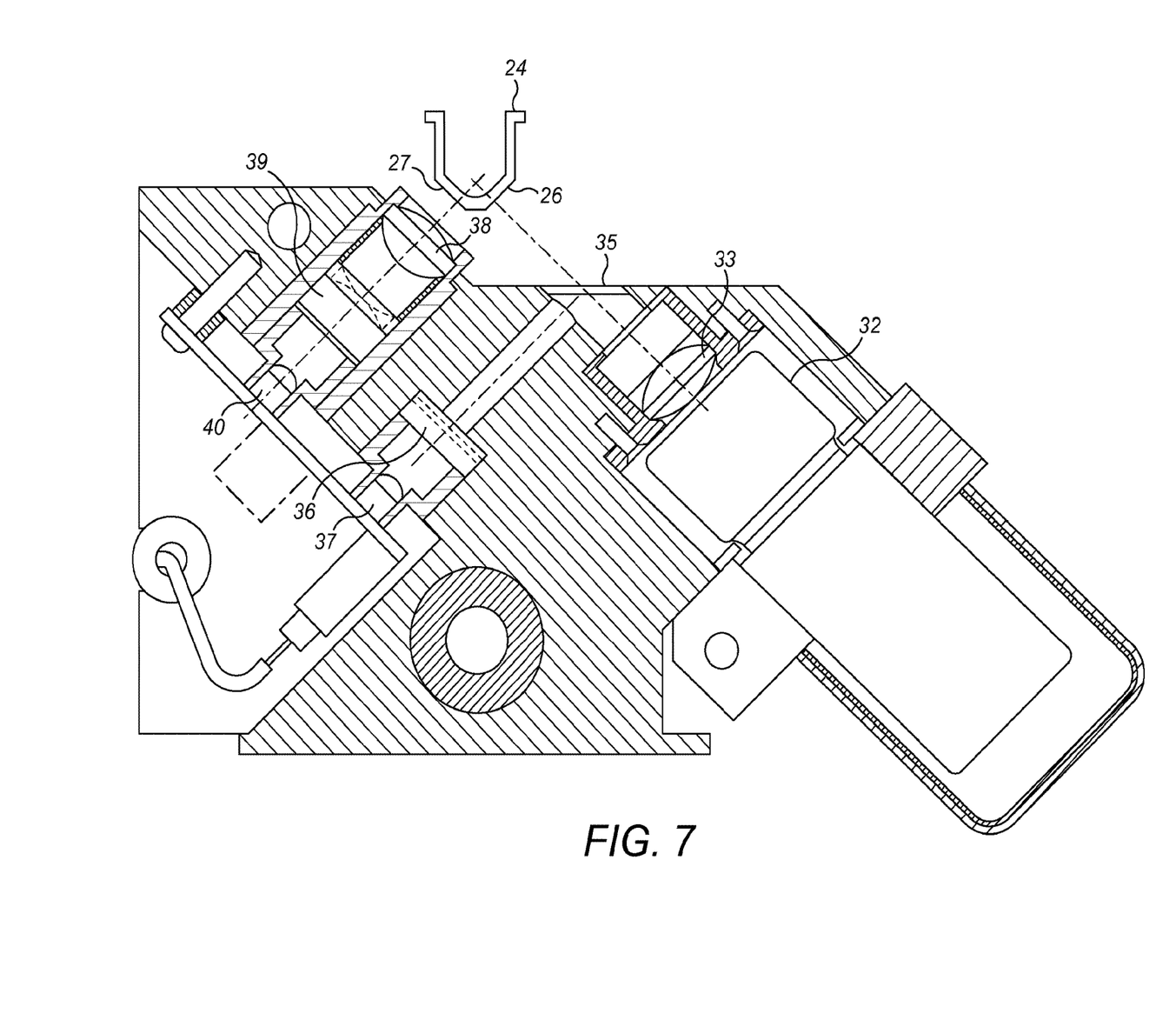
FIG. 7 shows a cross-section of the optical device according to FIG. 6, according to an embodiment of the invention, by way of example.

When the analysis well strip 20 is inserted onto a rail 12, only the last well 24 protrudes from the rail 12 in order to make it possible for an optical device 30 shown in FIGS. 6 and 7 to be positioned to carry out the analysis of the reaction medium contained in the last well 24.

The analysis of the sample to be tested is based on an illumination step and a detection step as described below by means of the optical device 30 shown in FIGS. 6 and 7 and detailed below.

The sample to be tested is analysed using only the contents of the last well 24. Thus, the illumination of the contents of the last well 24 is performed on a first surface S1, shown in FIG. 4, of the last well 24. The first surface S1 comprises the inclined wall 26 and the edges 206 and 207 of the last well 24. The fluorescence signals emitted by the last well 24 are detected by considering the light emitted across a second surface S2, shown in FIG. 5, of the last well 24. Surface S2 comprises the inclined wall 27 and the edges 208 and 209. Surface S2 is opposite surface S1. The second surface S2 makes it possible to detect the fluorescence signals emitted during the illumination of the first surface S1.

The analysis well strip 20 is made from a specific plastic material, such as polypropylene. Thus, wells 22, 23 and 24 are also made of this specific plastic material. The specific plastic material makes it possible to efficiently conserve the liquids and other materials necessary for any biological analysis. This specific plastic material possesses physicochemical properties such as fluorescence. Thus, when the last well 24 undergoes an illumination on the first surface S1 comprising the wall 26 and the edges 206 and 207, this first surface S1 emits fluorescence signals. Every other surface of the last well 24 which has received excitation signals also emits fluorescence signals.

As shown in FIG. 6, the optical device 30 is situated inside the analysis device 1, on the same horizontal plane as the various rails 12. The optical device 30 can slide on a track 31, the direction of which is perpendicular to the direction of the rails 12. As shown in FIG. 6, the form of the optical device 30 is such that the optical device 30 is placed opposite walls 26 and 27 of the last well 24.

FIG. 7 shows the various elements located inside the optical device 30.

The optical device 30 comprises a light source 32 such as a light-emitting diode (LED) which emits light signals or excitation beams. The light source 32 comprises any monochromatic source corresponding to the wavelength of the excitation peak of the chemical molecule used as a marker, such as a wavelength of 370 nm for 4-methylumbelliferone. The beam from the light source is of a thickness of around the thickness of the wall, and may be slightly less than the thickness of the wall. For example, the width of the beam is of around one millimetre. The light source 32 produces, for example, 200 brief illuminations or flashes spaced at 100 ms as the optical device 30 moves along the track 31. While the optical device 30 is in operation, the light source 32 lights the wall 26 of the last well 24. Insofar as the optical device 30 is movable on the track 31, the light source 32 can therefore emit several excitation beams illuminating various zones of the first surface S1 comprising the walls 26, 206, 207. The various illuminated zones correspond to the various positions of the optical device 30 on the track 31.

Figure 8:
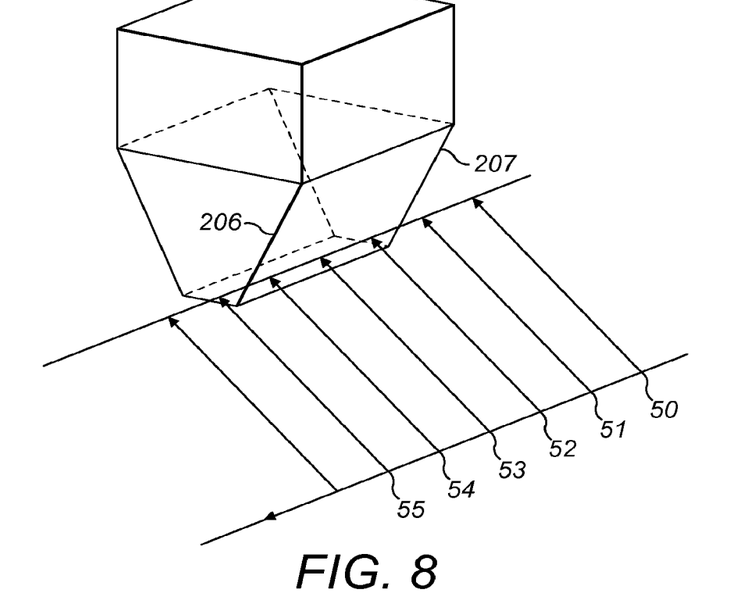
FIG. 8 shows the various positions of the optical device according to FIGS. 6 and 7, during the step of illuminating the reaction medium located in the last well according to FIGS. 2 and 3, according to an embodiment of the invention, by way of example.

Before the first surface S1, the light source 32 produces a series of emissions of excitation beams as the optical device 30 travels. Thus, the emission of the excitation beams is produced successively, for a first specific surface S1 as shown in FIG. 8 with the positions referenced from 50 to 55. Each emission of an excitation signal can be categorised as follows:

1) emission in the air, i.e. before the first edge 207 of the wall 26;
2) on the first edge 207 of the wall 26;
3) on the wall 26;
4) on the second edge 206 of the wall 26;
5) in the air, i.e. after the second edge 206 of the wall 26.

Thus, the optical device 30 can travel along the track 31 in order to operate on the various last wells 24 of each analysis well strip 20 present in the various rails 12 within the various receptacles 10.

An electronic control device (not shown), such as a computer, located in the analysis device 1 makes it possible to control the light source 32 in order to emit excitation beams at a predetermined frequency and a predetermined intensity. The electronic control device comprises a power source (not shown) and a control circuit (not shown) in order to trigger the emission of the excitation beams.

The electronic control device calculates the average value of the values relating to the measuring of the fluorescence signals detected. Thus, the electronic control device can compensate for any variations of intensity of the light source 32, for example due to the ageing of the light source.

The optical device 30 also comprises an optical element 33 such as an aspheric lens 33 for projecting the excitation beams onto the wall 26.

The optical device 30 comprises an optical separator 35 such as a semi-silvered mirror in order to reflect the excitation signal coming from the light source 32.

The optical device 30 also comprises an ultra-violet (UV) filter 36 in order to filter UV rays during the reflection of the excitation beam. The UV filter 36 is associated with a reference photodiode 37 which receives the signal reflected after transmission through the UV filter 36. Thus, the reference photodiode 37 produces an electrical signal proportional to the light intensity of the excitation beam.

The optical device 30 also comprises an aspheric lens 38 centred on the centre of the last well 24 and positioned at an angle of 90° relative to the direction of the excitation beam. Thus, the aspheric lens 38 can receive the fluorescence signals emitted, in particular, by the material and the contents of the last well 24. The second surface S2 of the last well 24 also emits fluorescence signals, in reaction to the illumination of the first surface S1 by the light source 32.

The optical device 30 also comprises a narrow-bandwidth filter 39 in order to limit the detection to a fluorescence signal with a wavelength of 450 nm, for example.

The optical device 30 also comprises a detection means 40 such as a high-sensitivity photodiode in order to detect the quantity of fluorescence emitted by the sample to be tested contained in the last well 24, and by the second surface S2 comprising the wall 27 of the last well 24 and the edges 208 and 209.

Figure 9:
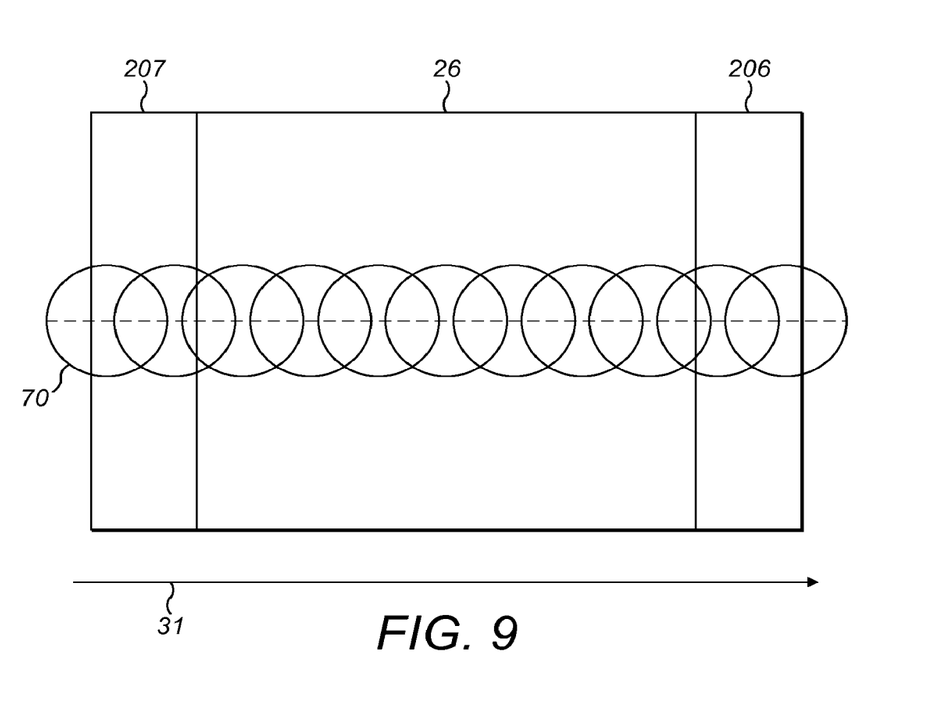
FIG. 9 shows a front view of a surface of the last well of the analysis well strip with a schematic representation of the form of the various excitation beams on this surface during the step of illuminating the reaction medium, according to an embodiment of the invention, by way of example.

As shown in FIG. 9, the light source 32 can emit circular, or substantially circular, excitation beams as shown by the circular shape 70. During the illumination of a given last well 24, the light source 32 of the optical device 30 emits several excitation beams located on the first surface S1 comprising the edge 206, the wall 26, the edge 207 of a last well 24. The excitation beams exhibit zones of intersection in order to guarantee an illumination of the surface S1 over the entire length of this surface S1.

As the optical device 30 travels, the light source 32 simultaneously dynamically emits the excitation beams in order to sweep the whole of the first surfaces S1 comprising the edge 206, the wall 26 and the edge 207 of the last wells 24 for each analysis well strip 20.

Figure 11:
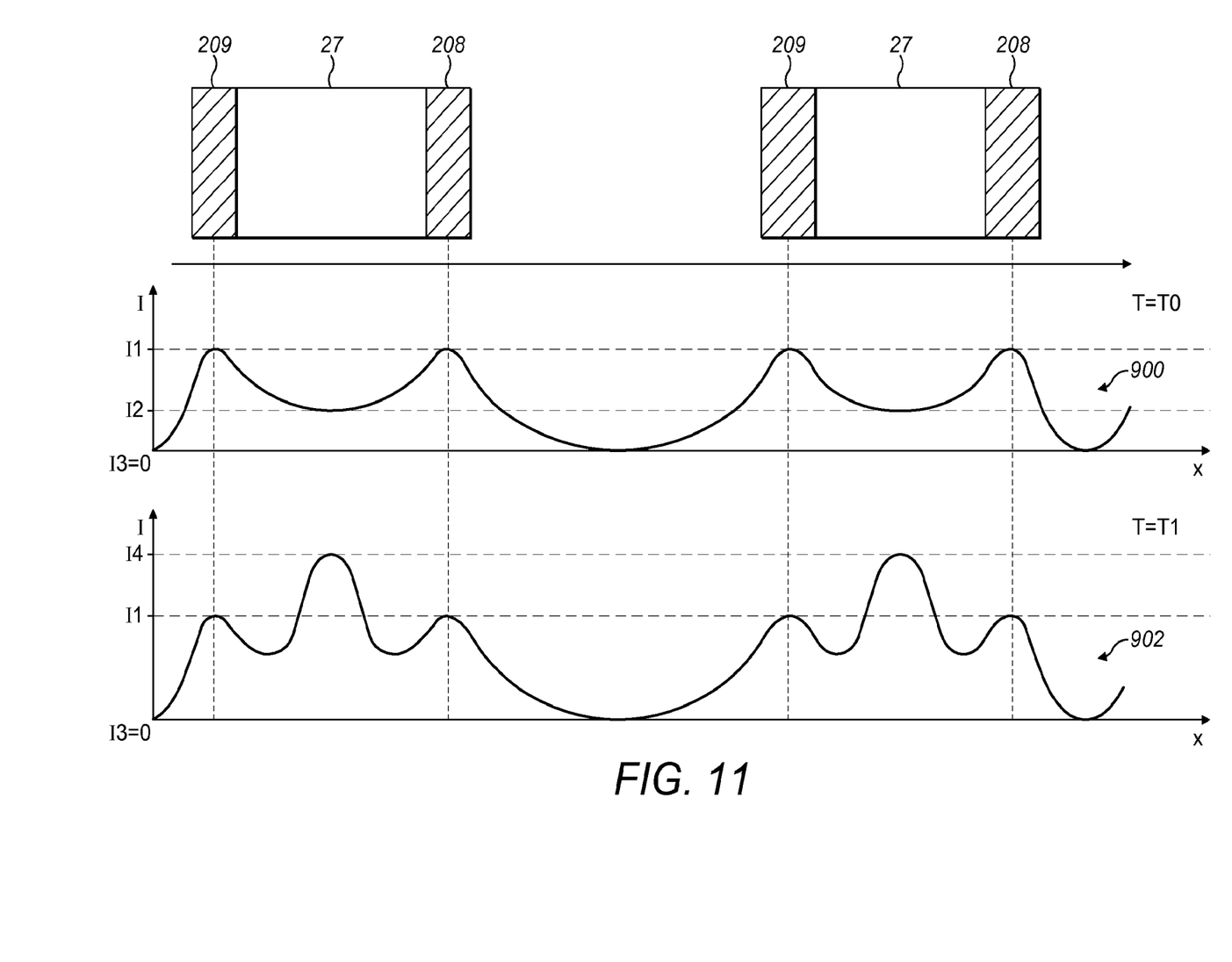
FIG. 11 shows two graphic representations relating to the intensity of the fluorescence signals concerning two last wells of two adjacent analysis well strips, the fluorescence signals being emitted by a surface of a last well and by the reaction medium, depending on the location of the optical device emitting the excitation beams, according to an embodiment of the invention, by way of example.

As shown in FIG. 11, the optical device 30 makes it possible to light various last wells 24 located within various analysis well strips 20 placed on various rails 12. FIG. 11 shows two second surfaces S2 relating to two last wells 24. Given the nature of the material of last well 24, the second surface S2 comprising the edges 208, 209 and the wall 27 emits fluorescence signals in reaction to the excitation beams received on the first surface S1. Insofar as the edges 208 and 209 are thicker than the wall 27, the fluorescence signals emitted by the edges 208 and 209 have an intensity greater than the intensity of the fluorescence signals emitted by the wall 27.

A signal processing device (not shown) located in the analysis device 1 and connected to the optical device 30 makes it possible to calculate various data relating to the fluorescence signals emitted by the edges 208, 209 and the wall 27, such as relative fluorescence units (RFU).

Various steps take place successively during the progression of the method of analysing the samples to be tested which are located in the corresponding last wells 24.

Figure 10:
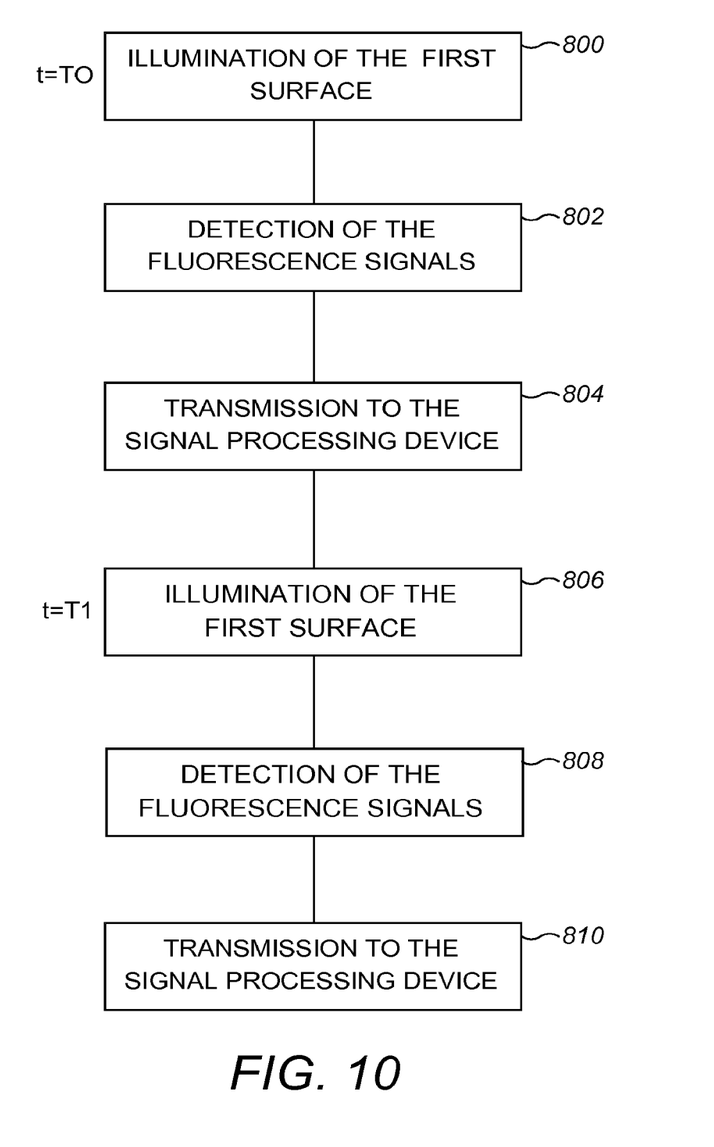
FIG. 10 shows the various steps of a method according to an embodiment of the invention, by way of example.

Thus, as indicated in FIG. 10, at a moment t=T0, the optical device 30 carries out a step 800 of illumination on the first surface S1 of the last well 24, while the optical device 30 carries out a step 802 of detecting fluorescence signals emitted from the second surface S2 of the last well 24. These fluorescence signals have an intensity relative to the initial fluorescence value of the last illuminated well 24 and of the medium contained in the last well 24 before any reaction with the sample to be tested. Thus, at t=T0, the optical device 30 makes it possible to measure the blank substrate, i.e. measure the initial fluorescence value of the last well 24 before any reaction associated with the introduction of the reaction medium.

Then the detected fluorescence signals are transmitted to the signal processing device in a step 804. The graph in FIG. 11 represents the variations in intensity of the fluorescence signals emitted by the second surface S2 comprising the edges 208, 209 and the wall 27 in response to illumination of the two last wells 24, under an emission of the light beams as shown in FIG. 9.

On the graph in FIG. 11, the fluorescence signals emitted by the edges 208 and 209 reach an intensity I1. The wall 27 also emits a fluorescence signal which reaches an intensity I2 which is lower than the intensity I1. This intensity value I2 corresponds to the value of the fluorescence value emitted at the centre of the wall 27.

Three fluorescence signals are generally distinguished depending upon the location of the excitation beam:

the fluorescence signal emitted in response to the excitation beam located at the entry of the wall 26, i.e. in proximity to a first edge 207;
the fluorescence signal emitted in response to the excitation beam located at the centre of the wall 26;
the fluorescence signal emitted in response to the excitation beam located at the exit of the wall 26, i.e. in proximity to a second edge 206.

The signal processing device makes it possible to determine the intensity value of the fluorescence signal at the centre of the wall 27, i.e. at the centre of the last well 24.

As the edges 208 and 209 are thicker than the wall 26, the intensity I1 of the fluorescence signal emitted by an edge 208 or 209 is greater than the intensity I2 of the fluorescence signal emitted by the wall 27. Finally, between the two last wells 24, the fluorescence signal reaches an intensity I3 which is lower than intensity I2. This fluorescence signal corresponds to the noise generated by the interference emissions from particles located in the space between the two last wells 24. This variable-intensity fluorescence signal corresponds to the background noise in the absence of any immunological reaction. In the absence of background noise, the intensity I3 has a value of 0.

At a moment t=T1, the reaction medium obtained after the sequence of reactions between the analyte potentially present in the sample to be tested and all of the reagents and/or solutions from one or more wells 23 is placed into each of the last wells 24. The reaction medium then contains a reaction product produced by the combination of the various reactions due to the reagents or to the solutions from the wells 23. Two of these last wells 24 are represented in FIG. 11. As indicated in FIG. 11, at t=T1, the optical device 30 then carries out an illumination step 806 and a detection step 808 similar to steps 800 and 802 as shown at the moment t=T0. Then, the fluorescence signals emitted are transmitted to the signal processing device 810, similar to step 804.

The signal 902 in FIG. 11 represents the variations in intensity of the fluorescence signals emitted in response to illumination of the two last wells 24, according to an emission of the excitation beams as shown in FIG. 9.

The signal 902 shows that the fluorescence signals emitted by edges 208 and 209 reach an intensity I1 substantially equal to the intensity I1 measured on signal 900. Similarly, the fluorescence signal emitted in the space situated between the two last wells 24 reaches an intensity I3 which is strictly equal to the intensity I3 measured on the signal. This intensity I3 corresponds to a zero fluorescence value of the two last wells. The fluorescence signal from the wall 27 comprises the fluorescence signal emitted both by the first surface S1 comprising the edges 206 and 207 and the wall 26, and by the second surface S2 comprising the edges 208 and 209 and the wall 27, and the fluorescence signal emitted by the reaction medium depending upon the quantity of analyte present in the sample to be tested.

The sum of these combined fluorescence signals produces an intensity I4 greater than the intensity I2 measured on the signal 900 if the analyte is present in the sample to be tested. Thus, we obtain a measurement of the quantity of fluorescence emitted at the end of reaction for a specific analysis defined by relative fluorescence units (RFU).

The signal processing device subtracts signal 900 and signal 902. The difference obtained between signal 900 at t=T0 and signal 902 at t=T1 makes it possible to determine the fluorescence value coming from the analyte present in the sample to be tested. Thus, the signal processing device makes it possible to precisely determine the intensity value relating solely to the sample and more precisely to the reaction product, in the absence of any interfering signal such as the fluorescence signals from the edges 208, 209 and the walls 27. The reaction product produces a fluorescence signal proportional or inversely proportional to the concentration of this reaction product within the sample. Therefore, we obtain a measurement of the quantity of relative fluorescence (RFV: Related Fluorescence Value) representative of this sample.

Figure 12:
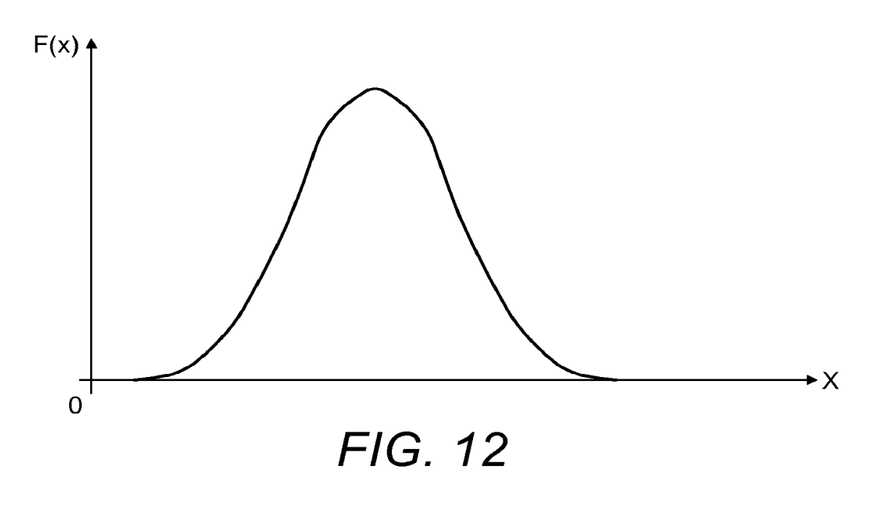
FIG. 12 shows a graph representing a profile of the lighting signal from a light source such as a light-emitting diode (LED), according to an embodiment of the invention, by way of example.

Alternatively, the signal processing device can also perform a deconvolution operation on signal 902. Indeed, the lighting profile F(x) of light source 32 which generates the excitation beam is as represented in FIG. 12. Moreover, the fluorescence signal profile G(x) generated by the edges 208, 209, and the wall 27 of the well 24 in the situation in which they are lit by a point-shaped source is as represented in FIG. 13.

Figure 13:
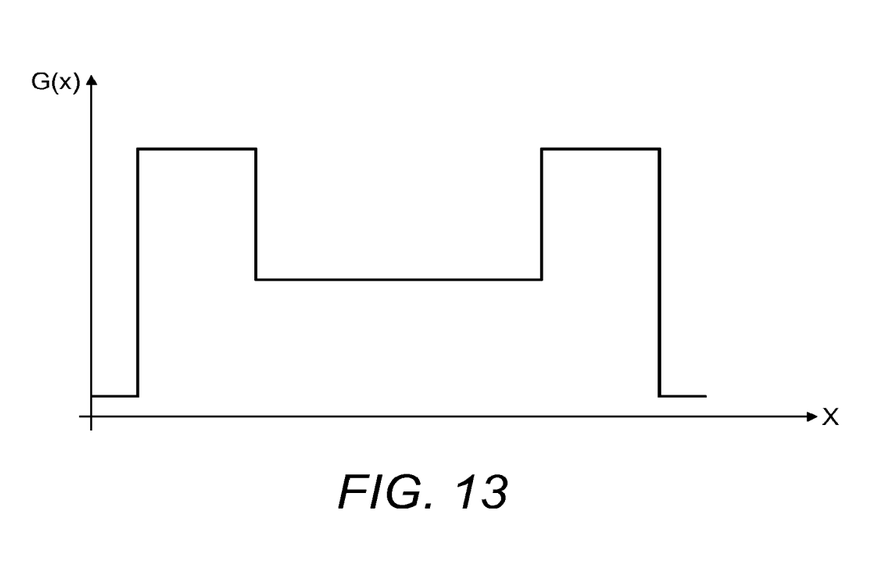
FIG. 13 shows a graph representing a profile of the fluorescence signal emitted by a wall of the last well according to FIG. 3, when this wall is lit by a point-shaped light source, according to an embodiment of the invention, by way of example.

At t=TO, the optical device 30 therefore detects a signal 900 which represents the convolution product of the signal generated by the light source 32 as in FIG. 12 and of the fluorescence emission profile of the well as in FIG. 13. Thus, when the optical device 30 at t=T1 detects the signal 902 as represented by the graph illustrated in FIG. 11, the signal represents the convolution product of the fluorescence emission profile of the well and of the fluorescence emission profile of the analyte present in the sample within the reaction medium.

The signal processing device can also apply a deconvolution operation to the signal 902 in order to obtain the fluorescence emission profile generated by the wall 27 of the well and the analyte present in the sample to be tested. In the absence of a deconvolution operation, the exploitable useful fluorescence signal is restricted to a location which corresponds to the middle of the wall 27 of the last well 24. Indeed, the exploitable useful fluorescence signal profile is altered by the width of the excitation beam as is shown by the profile of the signal 900 represented in FIG. 11. Conversely, performing an operation of deconvoluting the signal 902 by the lighting profile F(x) of the light source makes it possible to extract the fluorescence signal produced solely by the edges 208 and 209 of the last well 24. Thus the width of the exploitable useful fluorescence signal is augmented. Using the profiles resulting from the same deconvolution operation at t=T0 and at t=T1, it is possible to eliminate the contribution of the edges 208 and 209 from the measured signal 902.

Also, according to another object of the invention, the method according to the invention employs an operation of deconvoluting the fluorescence emission, generated by a well, by the lighting profile of a light source, i.e. by the spatial distribution of light intensity.

The present invention makes it possible to also resolve the problems of setting the position of the optical device 30 relative to the various analysis well strips 20. Indeed, the user no longer needs to correctly position the optical device so that the light source 32 specifically illuminates the first surface S1 in line with the width of the excitation beam.

The present invention also makes it possible to improve the reading sensitivity, insofar as the various signals produced make it possible to determine the nature of the fluorescence signals detected. Thus the user can easily separate the fluorescence signals from well 24 from the fluorescence signals coming from the reaction medium comprising the reaction product. Thus, it becomes apparent that, with a narrower excitation beam such as the beam from a light-emitting diode, the present invention makes it possible to reproduce the effects of a wide excitation beam from a light source such as a xenon bulb whilst avoiding the disadvantages of such a source with a wide excitation beam Using deconvolution, the present invention makes it possible to augment the widening of the useful zone of the fluorescence signal when employing the measured fluorescence signals. Thus, fluorescence signals generated by interfering elements such as bubbles and/or artefacts present within the well in question are not taken into account for the sample analysis.

The invention claimed is:

1. A system of analyzing a sample to be tested to determine the presence of or to quantify an analyte in the sample by employing a reaction which produces a reaction medium derived from the sample and possessing fluorescence properties, the reaction medium being located within a well, the reaction medium and the well forming an analysis assembly which possesses fluorescence properties, the system comprising:
    an optical device comprising a light source movable with respect to a surface of the well comprising a wall, a first edge of the wall, and a second edge of the wall, the optical device being configured to illuminate the analysis assembly by emitting excitation beams at different positions of the light source including at a position for the wall of the well, a position for the first edge of the wall, and a position for the second edge of the wall;
    a detection device configured to detect fluorescence emissions from the analysis assembly for each of the different positions of the light source including at the position for the wall of the well, the position for the first edge of the wall, and the position for the second edge of the wall; and
    a signal processing device configured to perform a calculation operation on:
    a first signal representing variations in intensity of the fluorescence emissions detected for each of the different positions of the light source including the position for the wall of the well, the position for the first edge of the wall, and the position for the second edge of the wall, in response to illumination and before introduction of the reaction medium into the well; and
    a second signal representing variations in intensity of the fluorescence emissions detected for each of the different positions of the light source including the position for the wall of the well, the position for the first edge of the wall, and the position for the second edge of the wall, in response to illumination and after introduction of the reaction medium into the well,
    thereby producing a resulting signal for each of the different positions of the light source including the position for the wall of the well, the position for the first edge of the wall, and the position for the second edge of the wall, and corresponding to the emission of a fluorescence signal produced solely by the reaction medium.

2. The system of claim 1, wherein the optical device is configured to illuminate at least a position before the first edge of the wall of the well, the first edge of the wall, the wall, the second edge of the wall, and a position after the second edge of the wall.

3. The system of claim 1, wherein the detection device is configured to detect the fluorescence emissions with respect to a second surface of the well that is opposite to the surface of the well that is illuminated.

* * * * *